United States Patent
Nouri et al.

(10) Patent No.: US 11,402,901 B2
(45) Date of Patent: Aug. 2, 2022

(54) DETECTING EYE MEASUREMENTS

(71) Applicant: Hewlett-Packard Development Company, L.P., Spring, TX (US)

(72) Inventors: Joseph Nouri, Fort Collins, CO (US); Eric Bokides, Fort Collins, CO (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 17/056,866

(22) PCT Filed: Mar. 22, 2019

(86) PCT No.: PCT/US2019/023585
§ 371 (c)(1),
(2) Date: Nov. 19, 2020

(87) PCT Pub. No.: WO2020/197537
PCT Pub. Date: Oct. 1, 2020

(65) Prior Publication Data
US 2021/0405741 A1 Dec. 30, 2021

(51) Int. Cl.
*G06F 3/01* (2006.01)
*G06V 40/18* (2022.01)
*G06K 9/62* (2022.01)

(52) U.S. Cl.
CPC ........... *G06F 3/013* (2013.01); *G06K 9/6256* (2013.01); *G06V 40/193* (2022.01); *G06F 2203/011* (2013.01)

(58) Field of Classification Search
CPC . G06F 3/013; G06F 2203/011; G06K 9/6256; G06V 40/193
See application file for complete search history.

(56) References Cited

U.S. PATENT DOCUMENTS

| | | | |
|---|---|---|---|
| 8,878,749 B1 | 11/2014 | Wu et al. | |
| 10,126,815 B2* | 11/2018 | Vidal | G01S 17/88 |
| 10,163,010 B2 | 12/2018 | Kaehler et al. | |
| 2008/0226138 A1* | 9/2008 | Suzuki | G06T 7/12 |
| | | | 382/117 |
| 2009/0003709 A1* | 1/2009 | Kaneda | G06V 20/597 |
| | | | 382/190 |
| 2010/0094176 A1* | 4/2010 | Ohue | A61B 3/14 |
| | | | 600/595 |
| 2012/0021806 A1* | 1/2012 | Maltz | G02B 27/017 |
| | | | 455/566 |

(Continued)

OTHER PUBLICATIONS

Vahid Kazemi, Josephine Sullivan; "One Millisecond Face Alignment with an Ensemble of Regression Trees" The IEEE Conference on Computer Vision and Pattern Recognition (CVPR), 2014, pp. 1867-1874.

*Primary Examiner* — Mihir K Rayan
(74) *Attorney, Agent, or Firm* — HP Inc. Patent Department (57) ABSTRACT

In various examples, a plurality of reference points may be generated by processing an image of an eye of a user from a vision sensor. The plurality of reference points may correspond to, for example, a boundary between a sclera of the eye and an eyelid of the user, a boundary between a pupil and a cornea, etc. Based on the reference points corresponding to the boundary between the sclera and the eyelid, a measure of the eye of the user may be detected.

12 Claims, 6 Drawing Sheets

(56) References Cited

U.S. PATENT DOCUMENTS

| | | |
|---|---|---|
| 2013/0101225 A1* | 4/2013 | Kadoya ............... G06V 10/451 |
| | | 382/199 |
| 2013/0281798 A1 | 10/2013 | Rau et al. |
| 2014/0072230 A1* | 3/2014 | Ruan .................... G06V 40/193 |
| | | 382/199 |
| 2017/0231490 A1 | 8/2017 | Toth et al. |
| 2017/0278122 A1 | 9/2017 | Kaehler |
| 2017/0322679 A1 | 11/2017 | Gordon |
| 2017/0365101 A1 | 12/2017 | Samec et al. |
| 2018/0096198 A1 | 4/2018 | Tzvieli et al. |
| 2018/0096503 A1 | 4/2018 | Kaehler et al. |
| 2018/0140180 A1 | 5/2018 | Coleman |
| 2018/0190011 A1 | 7/2018 | Platt et al. |
| 2018/0300589 A1 | 10/2018 | Levinshtein et al. |
| 2019/0235247 A1* | 8/2019 | Norden .................... G01V 8/22 |
| 2019/0370959 A1* | 12/2019 | Krishna .................... G06T 7/60 |

* cited by examiner

DETECTING EYE MEASUREMENTS

BACKGROUND

With some types of immersive computing, an individual wears a head-mounted display ("HMD") in order to have an augmented reality ("AR") and/or virtual reality ("VR") experience. Eye tracking is an element of immersive computing that enables features such as user selection of virtual objects rendered in a VR landscape. Eye tracking may also be used outside of the context of immersive computing.

BRIEF DESCRIPTION OF THE DRAWINGS

Features of the present disclosure are illustrated by way of example and not limited in the following figure(s), in which like numerals indicate like elements.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Additionally, it should be understood that the elements depicted in the accompanying figures may include additional components and that some of the components described in those figures may be removed and/or modified without departing from scopes of the elements disclosed herein. It should also be understood that the elements depicted in the figures may not be drawn to scale and thus, the elements may have different sizes and/or configurations other than as shown in the figures.

Figure 1:
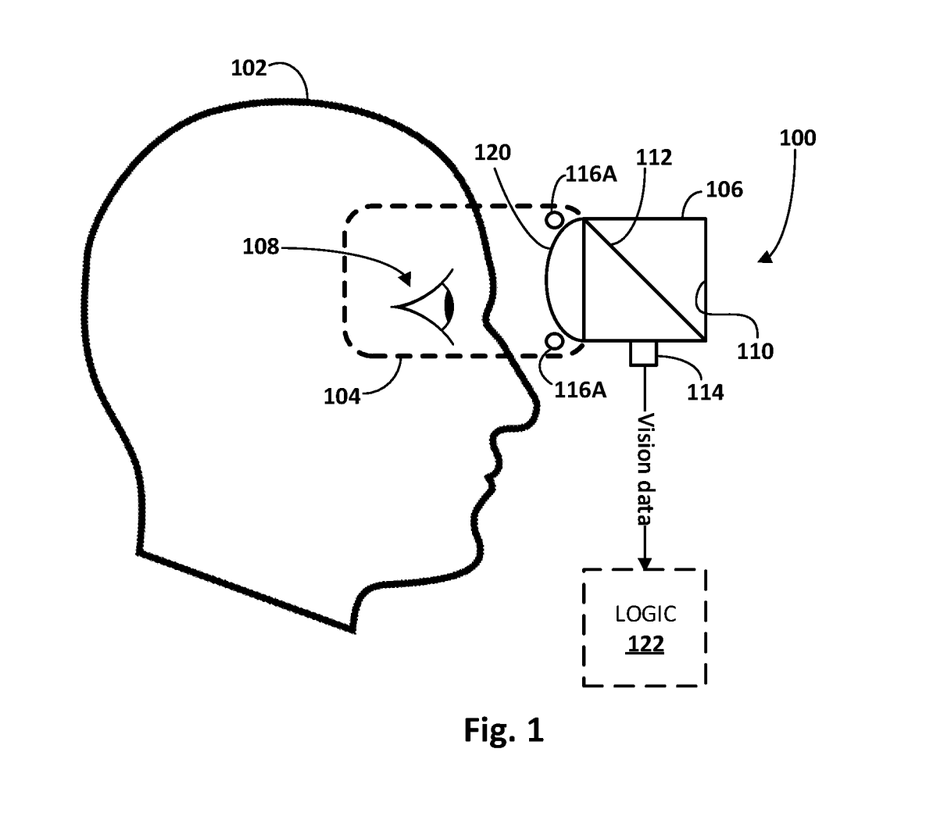
FIG. 1 depicts an example environment in which selected aspects of the present disclosure may be implemented.

Referring now to FIG. 1, an example head-mounted display ("HMD") 100 configured with selected aspects of the present disclosure is depicted schematically as it might be worn by an individual 102, which in the present context may also be referred to as a "user" or "wearer." In FIG. 1, HMD 100 includes a first housing 104 and a second housing 106. However, in other examples, other housing configurations may be provided. First housing 104 encloses, among other things, an eye 108 of individual 102, which in this case is the individual's right eye. Although not visible in FIG. 1 due to the viewing angle, in many examples, first housing 104 may also enclose another eye of individual 102, which in this case would be the individual's left eye.

Second housing 106 may include at least some of the electronics of HMD 100 that are operable to provide individual 102 with an immersive computing experience. For example, in FIG. 1, second housing 106 includes at least one display 110, which in many cases may include two displays, one for each eye 108 of individual 102, that collectively render content in stereo. By rendering virtual content on display 110, HMD 100 provides individual 102 with a VR-based immersive computing experience in which individual 102 may interact with virtual objects, e.g., using his or her gaze. In some such examples, first housing 104 may completely enclose the eyes of individual 102, e.g., using a "skirt" or "face gasket" of rubber, synthetic rubber, silicone, or other similar materials, in order to prevent outside light from interfering with the individual's VR experience.

In some examples, HMD 100 may provide individual 102 with an augmented reality experience. For example, display 110 may be transparent so that individual 102 may see the physical world beyond display 110. Meanwhile, display 110 may be used to render virtual content, such as visual annotations of real world objects sensed by an external camera (not depicted) of HMD 100. In some such examples, HMD 100 may take the form of a pair of "smart glasses" with a relatively compact and/or light form factor. In some such examples, various components of FIG. 1 may be omitted, sized differently, and/or arranged differently to accommodate the relatively small and/or light form factor of smart glasses.

In some examples, including that of FIG. 1, second housing 106 includes a mirror 112 that is angled relative to second housing 106. Mirror 112 is tilted so that a field of view ("FOV") of a vision sensor 114 is able to capture eye 108 of individual 102. Light sources 116A and 116B are also provided, e.g., in first housing 104, and may be operable to emit light that is reflected from eye 108 to mirror 112, which redirects the light towards vision sensor 114.

Vision sensor 114 may take various forms. In some examples, vision sensor 114 may be an infrared ("IR") camera that detects electromagnetic radiation between 400 nm to 1 mm, or, in terms of frequency, from approximately 430 THz to 300 GHz. In some such examples, light sources 116 may take the form of IR light-emitting diodes ("LED"). Additionally, mirror 112 may be specially designed to allow non-IR light to pass through, such that content rendered on display 110 is visible to eye 108, while IR light is reflected towards vision sensor 114. For instance, mirror 112 may take the form of a dielectric mirror, e.g., Bragg mirror. In some examples, mirror 112 may be coated with various materials to facilitate IR reflection, such as silver or gold. In other examples, vision sensor 114 (and light source 116A/B) may operate in other spectrums, such as the visible spectrum, in which case vision sensor 114 could be an RGB camera.

The example of FIG. 1 is not meant to be limiting, and vision sensor 114, or multiple vision sensors, may be deployed elsewhere on or within HMD 100. In some examples, increasing the number of vision sensors may increase the accuracy of techniques described herein and/or the measurements they generate. In some examples, two vision sensors may be deployed, one for each eye of individual 102.

In some examples, various optics 120 may be provided, e.g., at an interface between first housing 104 and second housing 106. Optics 120 may serve various purposes and therefore may take various forms. In some examples, display 110 may be relatively small, and optics 120 may serve to magnify display 110, e.g., as a magnifying lens. In some examples, 120 optics may take the form of a Fresnel lens, which may be lighter, more compact, and/or most cost-effective than a non-Fresnel magnifying lens. Using a Fresnel lens may enable first housing 104 and/or second housing 106 to be manufactured into a smaller form factor.

HMD 100 may facilitate eye tracking in various ways. In some examples, light sources 116A-B may emit light into first housing 104. This emitted light may reflect from eye 108 in various directions, including towards mirror 112. As explained previously, mirror 112 may be designed to allow light emitted outside of the spectrum of light sources 116A-B to pass through, and may reflect light emitted within the spectrum of light sources 116A-B towards vision sensor 114. Vision sensor 114 may capture vision data that is then provided to logic 122 that is integral with, or remote from, HMD 100. Vision data may take the form of, for example, a sequence of images captured by vision sensor 114. Logic 122 may perform various types of image processing on these images to determine various aspects of eye 108, such as its pose (or orientation), pupil dilation, pupil orientation, a measure of eye openness, etc.

Logic 122 may take various forms. In some examples, logic 122 may be integral with HMD 100, and may take the form of a processor (or multiple processors) that executes instructions stored in memory (not depicted). For example, logic 122 could include a central processing unit ("CPU") and/or a graphics processing unit ("GPU"). In some examples, logic 122 may include an application specific integrated circuit ("ASIC"), a field-programmable gate array ("FPGA"), and/or other types of circuitry that are operable to perform logic operations. In this manner, logic 122 may be circuitry or a combination of circuitry and executable instructions.

In other examples, logic 122 may not be integral with HMD 100. In some examples, logic 122 may be integral with another device operated by individual 102, such as a smart phone, smart watch, laptop computer, desktop computer, set top box, a remote server forming part of what is commonly referred to as the "cloud," and so forth. For example, logic 122 may include a processor of a smart phone carried by individual 102. Individual 102 may operably couple the smart phone with HMD 100 using various wired or wireless technologies, such as universal serial bus ("USB"), wireless local area networks ("LAN") that employ technologies such as the Institute of Electrical and Electronics Engineers ("IEEE") 802.11 standards, personal area networks, mesh networks, high-definition multimedia interface ("HDMI"), and so forth. Once operably coupled, individual 102 may wear HMD 100, which may render content that is generated by the smart phone on display 110 of HMD 100. For example, individual 102 could install a VR-capable game on the smart phone, operably couple the smart phone with HMD 100, and play the VR-capable game through HMD 100.

Based on the aspects of eye 108 determined from the vision information generated by vision sensor 114, such as a pose of eye 108, logic 122 may determine a point or target on display 110 at which a fovea of eye 108 is directed. This point and its immediate surroundings on display 100 may encompass the specific rendered content on which individual 102 is most focused. The target of the individual's fovea on display 110 may be used, for instance, to render a cursor or other selection tool on display 110, e.g., so that individual 102 may move his eyes around to interact with content rendered on various portions of display 110. For example, to select a particular object rendered on display 110, individual 102 might look at the object and then perform some other action, such as blinking, pressing a button, staring at it for some predetermined amount of time (which may be akin to hovering), etc., in order to interact with the rendered object. This data may also be used for foveated rendering.

Existing eye tracking solutions either fail to provide sufficient information or utilize a relatively large amount of computing power, which in some cases may result in a relatively resource-constrained HMD delegating eye tracking computation to a remote computing device (e.g., the cloud). Accordingly, relatively low-cost techniques for determining various eye tracking-related features of an eye are described herein. In various examples, these techniques may be performable using logic 122 that is mostly or entirely onboard HMD 100. In some such examples, various machine learning models may be trained, e.g., remotely from HMD 100, to generate output that infers various aspects of eye 108 that are usable to perform eye tracking.

Figure 2:
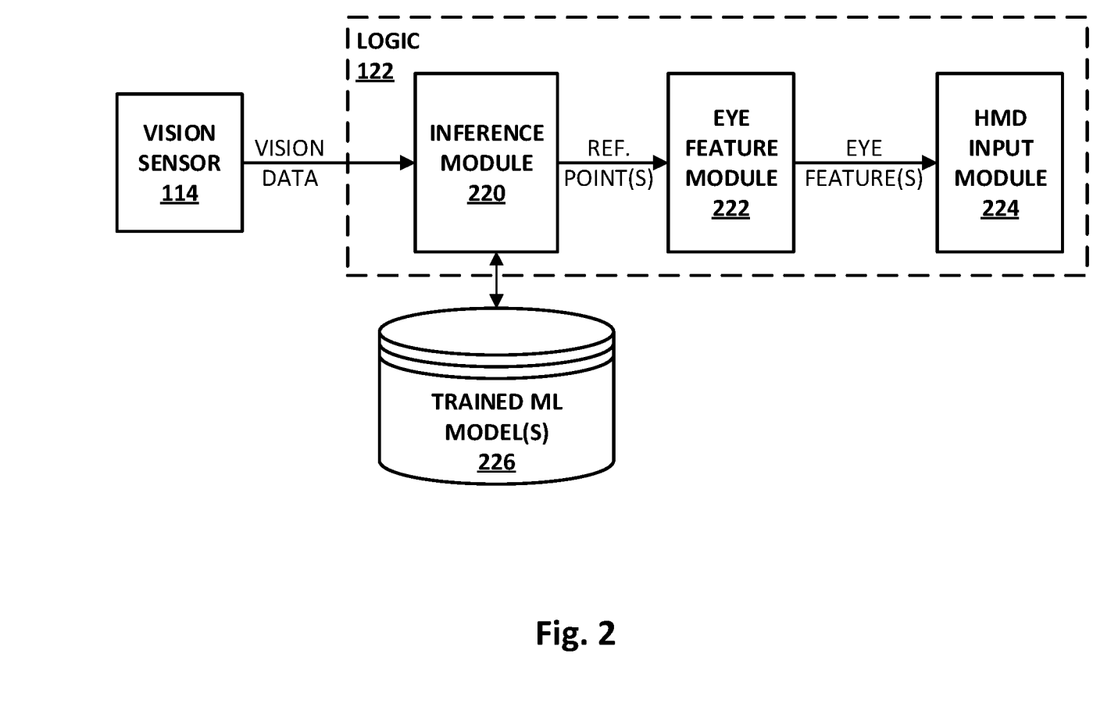
FIG. 2 demonstrates an example of how data may be processed from acquisition of image data to determination of eye pose and, ultimately, application of eye pose in a downstream process.

FIG. 2 schematically depicts one example of how data may be processed using relatively few computing resources to ascertain various eye-tracking-related features of eye 108. Vision sensor 114 provides the vision data it generates to logic 122, as described previously. As also noted previously, logic 122 may be hosted wholly or partially onboard HMD 100, on another computing device operated by individual 102, such as a smart phone, or remotely from individual 102 and HMD 100.

Logic 122 may operate various modules using any combination of circuitry or combination of circuitry and machine-executable instructions. For example, in FIG. 2, logic 122 operates an inference module 220, an eye feature module 222, and an HMD input module 224. In other examples, any one of modules 220-224 may be combined with other modules and/or omitted.

Inference module 220 applies all or selected parts of vision data received from vision sensor 114 as input across a trained machine learning model obtained from a trained machine learning model database 226 to generate output. The output generated based on the machine learning model may indicate various aspects of eye 108, such as a plurality of reference points of eye 108.

Database 226 may be maintained in whole or in part in memory of HMD 100. For example, machine learning model(s) in database 226 may be stored in non-volatile memory of HMD 100 until needed, at which point they may be loaded into volatile memory. As used herein, memory may refer to any electronic, magnetic, optical, or other physical storage device that stores digital data. Volatile memory, for instance, may include random access memory ("RAM"). More generally, memory may also take the form of electrically-erasable programmable read-only memory ("EEPROM"), a storage drive, an optical drive, and the like.

Various types of machine learning models may be trained and used, e.g., by inference module 220, to make various inferences about eye 108 based on the vision data. In some examples, the machine learning model may be a trained shape predictor model, such as an ensemble of regression tree models that may alternatively be referred to as cascaded regression trees, or more generally, a cascade of regression functions or "regressors." In some such examples, each regression function of the cascade of regression functions may be trained using a gradient boosting tree technique. In some examples, gradients of points on an image of eye 108 may be compared to fit a shape to the image of the eye. From that shape, it is possible to determine various features of the eye.

In some examples, the machine learning model may take other forms, such as a convolutional neural network ("CNN"), multiple machine learning models incorporated into an ensemble model, and so forth. More generally, a machine learning model may learn weights in a training stage utilizing various machine learning techniques as appropriate to the classification task, which may include, for example linear regression, logistic regression, linear discriminant analysis, principal component analysis, classification trees, naïve Bayes, k-nearest neighbors, learning vector quantization, support vector machines, bagging forests, random forests, boosting, AdaBoost, etc.

The plurality of reference points that were inferred by inference module 220 based on the machine learning model obtained from database 226 are provided to eye feature module 222. Eye feature module 222 employs various techniques and/or heuristics to analyze the reference points and determine various eye-tracking-related features of eye 108. Examples of these features will be described in more detail in relation to FIGS. 3A-C and in FIGS. 4A-C.

The eye-tracking-related feature(s) determined by eye feature module 222 are provided to HMD input module 224. HMD input module 224 may take various actions based on the eye-tracking-related features it receives. In some examples, the eye-tracking-related feature(s) determined by eye feature module 222 may be packaged as an application programming interface ("API") state that corresponds to a state of eye 108. HMD input module 224 may then determine what action to take, if any, based on the eye's state.

Various eye features detected using techniques described herein may be employed for various purposes. An orientation of eye 108, such as whether it is looking up or down, left or right, may be used to for various purposes, such as changing an image processing focal point, launching or hiding a menu, navigating through multiple menus, interacting with a virtual object rendered on display 110, turning HMD 100 on or off, changing various HMD settings such as brightness, contrast, changing other output settings such as volume, and so forth.

A measure of pupil dilation and/or orientation may be used for a variety of purposes, such as estimating a mental or physical state of the user, including but not limited to anxiety, cognitive load, level of understanding, etc. A measure of eye openness may also be used to estimate a physical or mental state of the user. For example, if the user's measure of eye openness is less than an average measure of eye openness observed of the user (or some other threshold), that may suggest that the user is tired, that the content rendered on the display is bright enough to cause the user to reflexively squint, or that the rendered content is blurred or otherwise distorted, which may cause the user to squint in an attempt to make the imagery more clear. A greater-than-usual measure of eye openness may suggest a high level of concentration, surprise, interest, that the display is too dim, etc.

Figure 3A:
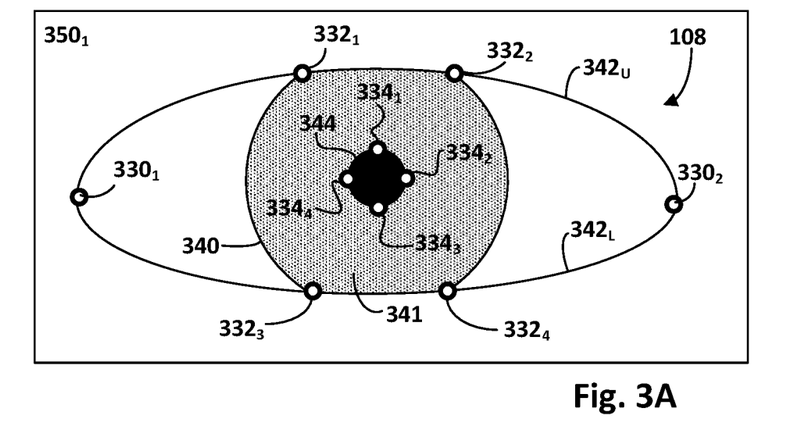
FIGS. 3A-C demonstrate an example of how disclosed techniques may be used to generate a plurality of reference points in an image of a user's eye.
Figure 3B:
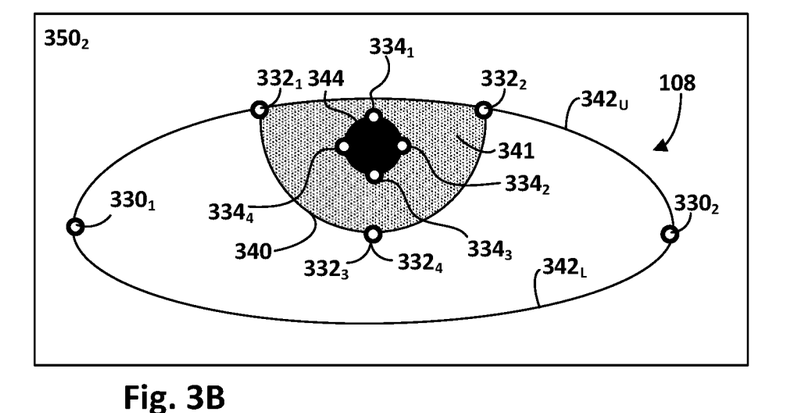
Figure 3C:
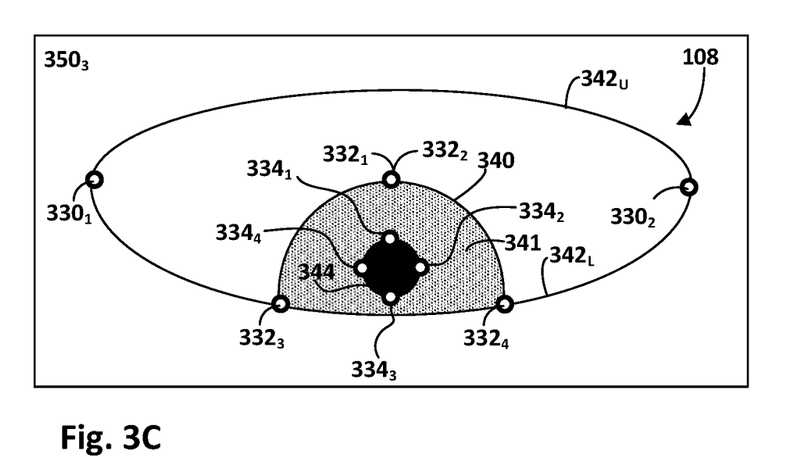

FIGS. 3A-C respectively depict three separate images $350_{1-3}$ of eye 108 captured by vision sensor 114. These images $350_{1-3}$ have been annotated with reference points corresponding to various visible features of eye 108. In some examples, when inference module 220 applies images $350_{1-3}$ as input across a trained machine learning model from database 226, these reference points may be generated as output. Each reference point may identify a particular point or pixel(s) on the respective image at which a particular visible feature of eye 108 is detected. Eye feature module 222 may utilize these reference points and/or spatial relationships between them to identify various eye-tracking-features of eye 108, such as its orientation, pupil dilation, pupil orientation, gaze direction, eye openness, and so forth.

In image $350_1$ of FIG. 3A, eye 108 is captured looking straight ahead. Reference point $330_1$ identifies a left extent of eye 108 and reference point $330_2$ identifies a right extent of eye 108. Reference points $330_{1-2}$ may correspond to, for instance, medial and lateral commissures of eye 108. Reference points $332_{1-4}$ correspond to intersections of a boundary or "limbus" 340 between a cornea 341 of eye 108 and an eyelid 342. More particularly, reference points $332_{1-2}$ correspond to intersections of limbus 340 and an upper eyelid $342_U$, and reference points $332_{3-4}$ correspond to intersections of limbus 340 and a lower eyelid $342_L$. Reference points $334_{1-4}$ correspond to various extents of a pupil 344 of eye 108. More particularly, reference point $334_1$ corresponds to a top extent of pupil 344, reference point $334_2$ corresponds to a right extent of pupil 344, reference point $334_3$ corresponds to a bottom extent of pupil 344, and reference point $334_4$ corresponds to a left extent of pupil 344.

Eye feature module 222 may use at least some of reference points $334_{1-4}$ to determine a measure of pupil dilation and/or orientation. For example, the distance between reference points $334_1$ and $334_3$ may be a vertical diameter of pupil 344, and may be proportionate to or otherwise represent a current measure of pupil dilation. In some examples, the distance between reference points $334_2$ and $334_4$ may be proportionate to or otherwise represent a horizontal diameter of pupil 344, and may also represent a current measure of pupil dilation. In some examples, and under the assumption that pupil or more or less circular, the horizontal diameter may be used to confirm the vertical diameter, or vice versa.

In FIG. 3A, in which image $350_1$ captures eye 108 looking straight ahead, limbus 340 intersects both upper eyelid $342_U$ and lower eyelid $342_L$. Consequently, reference points $332_1$ and $332_2$ are separated by some horizontal distance, and reference points $332_3$ and $332_4$ are also separated by some horizontal distance. Eye feature module 222 may utilize these distances to determine a vertical orientation of eye 108. For example, if these horizontal distances are relatively similar, e.g., within some predetermined threshold value of each other, then eye feature module 222 may determine that eye 108 is neither looking up nor down, but rather is likely looking straight ahead. In some examples, the distances between these reference points $332_{1-4}$ and one or both of reference points $330_{1-2}$ may also be used to determine vertical orientation.

These reference points $332_{1-4}$ and $330_{1-2}$ may also be usable, e.g., by eye feature module 222, to determine a horizontal orientation of eye 108. For example, a proportional distance of any one of points $332_{1-4}$ from reference point $330_1$ and $330_2$ may be used by eye feature module 222 as an indicator of horizontal orientation, i.e., whether the user is looking left or right, and by how much.

In contrast to FIG. 3A, in image $350_2$ of FIG. 3B, eye 108 is looking upward. And in image $350_3$ of FIG. 3C, eye 108 is looking downward. This orientation is captured in the spatial relationships between various reference points. For example, in FIG. 3B, reference points $332_1$ and $332_2$, which correspond to intersections between limbus 340 and upper eyelid $342_U$, are at a greater horizontal distance from each other than reference points $332_3$ and $332_4$, which correspond to intersections between limbus 340 and lower eyelid $342_L$. In fact, because limbus 340 does not intersect lower eyelid $342_L$ at all, reference points $332_3$ and $332_4$ are coincident. In some examples, eye feature module 222 may interpret this relatively large disparity between these horizontal distances as meaning eye 108 is oriented upward.

The opposite is true in FIG. 3C, in which a horizontal distance between reference points $332_3$ and $332_4$ is far greater than a horizontal distance between reference points $332_1$ and $332_2$. In fact, because limbus 340 does not intersect upper eyelid $342_U$ at all, reference points $332_1$ and $332_2$ are coincident. In some examples, eye feature module 222 may interpret this relatively large disparity between these horizontal distances as meaning eye 108 is oriented downward.

In some examples, the magnitude of the disparity between these horizontal distances may be used by eye feature module 222 to estimate a relative vertical orientation of eye 108. If the disparity is relatively large, as is the case in FIGS. 3B and 3C, then the vertical orientation of eye 108 may be estimated as strongly upward or downward, as applicable. On the other hand, if the magnitude of the disparity between these horizontal distances is relatively low, as was the case with FIG. 3A, then the vertical orientation estimated by eye feature module 222 may be closer to neutral.

Figure 4A:
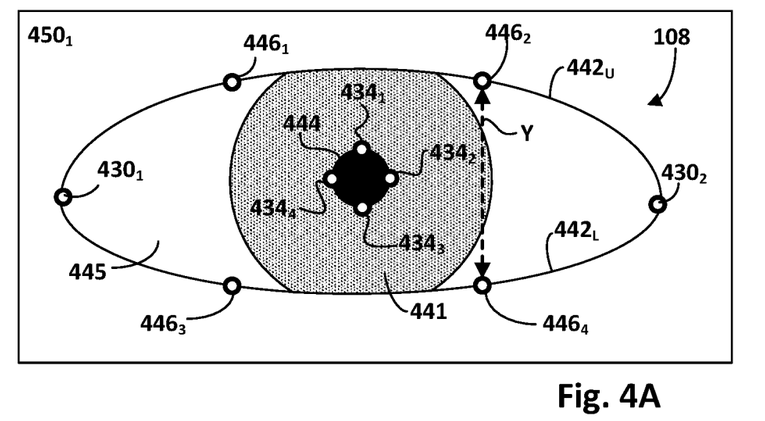
FIGS. 4A-C demonstrate another example of how disclosed techniques may be used to generate a plurality of reference points in an image of a user's eye.
Figure 4B:
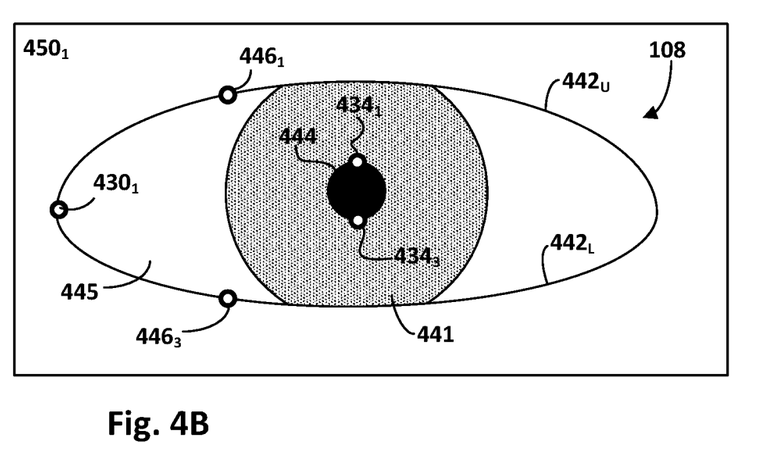
Figure 4C:
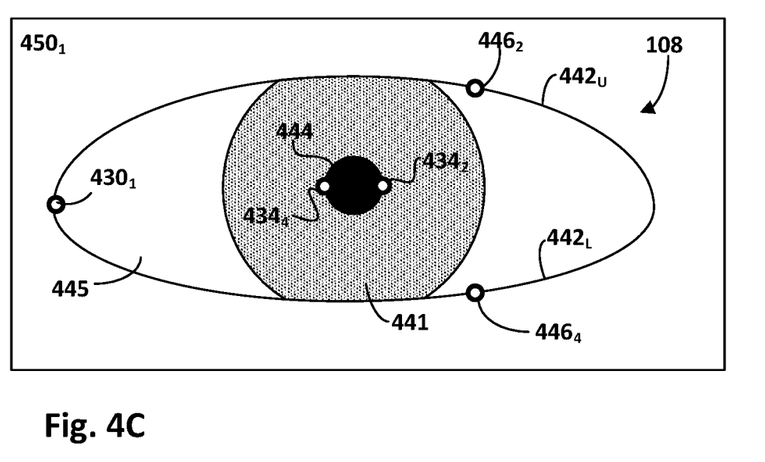

FIGS. 4A-C depict, respectively, three separate images $450_{1-3}$ of eye 108 captured by vision sensor 114. As was the case with images $350_{1-3}$ in FIGS. 3A-C, images $450_{1-3}$ have been annotated with reference points corresponding to various visible features of eye 108. In some examples, when inference module 220 applies images $450_{1-3}$ as input across a trained machine learning model from database 226, these reference points may be generated as output. Each reference point may identify a particular point or pixel(s) on the respective image at which a particular visible feature of eye 108 is detected. As was the case with the reference points of FIG. 3, eye feature module 222 may utilize reference points of FIG. 4 and/or spatial relationships between them to identify various eye-tracking-features of eye 108, such as its orientation, eye openness, pupil dilation, pupil orientation, gaze direction, and so forth.

Some of the reference points in FIGS. 4A-C are similar to those depicted in FIGS. 3A-C. For example, reference point $430_1$ identifies a left extent of eye 108 and reference point $430_2$ identifies a right extent of eye 108. Reference points $430_{1-2}$ may correspond to, for instance, medial and lateral commissures of eye 108. Reference points $434_{1-4}$ correspond to various extents of a pupil 444 of eye 108. More particularly, reference point $434_1$ corresponds to a top extent of pupil 444, reference point $434_2$ corresponds to a right extent of pupil 344, reference point $434_3$ corresponds to a bottom extent of pupil 444, and reference point $434_4$ corresponds to a left extent of pupil 444.

In FIGS. 4A-C, the sclera 445 of eye 108 is identified. Sclera 445 is the white part of eye 108 that surrounds the cornea 441. Various reference points $446_{1-4}$ along the boundary of eyelids $442_U$, $442_L$ and sclera 445 are also identified. Reference points $446_{1-2}$ are identified on the boundary of sclera 445 and upper eyelid $442_U$. Reference points $446_{3-4}$ are identified on the boundary of sclera 445 and lower eyelid $442_L$. Various combinations of reference points $446_{1-4}$ may be used to determine features of eye such as a measure of eye openness.

In some examples, reference points $446_{1-4}$ may be selected/identified based on their spatial relationships to each other and/or to other reference points. In FIG. 4, for instance, reference point $446_1$ is aligned vertically with reference point $446_3$. Likewise, reference point $446_2$ is aligned vertically with reference point $446_4$. Pairs of reference points <$446_1$, $446_3$> or <$446_2$, $446_4$> may be selected in some examples based on a distance of a vertical line (one example indicated at Y in FIG. 4A) between them and other extremes of eye 108, such as reference points $430_1$ and/or $430_2$. As a non-limiting example, the pair of reference points <$446_1$, $446_3$> may be spaced approximately ⅓ of the way across a horizontal span of eye 108 from reference point $430_1$. As another non-limiting example, the pair of reference points <$446_2$, $446_4$> may be selected so that the line Y between them in FIG. 4A is spaced approximately ⅓ of the way across a horizontal span of eye 108 from reference point $430_2$.

It is possible that in some scenarios, all reference points might not be readily identifiable. For example, when a Fresnel lens is employed it is possible that some portions of eye 108 may be distorted, making identification of some reference points challenging. Accordingly, techniques described herein may be used with less than all of the reference points depicted in FIG. 4A (or FIG. 3A) to determine features of eye 108.

In FIG. 4B, for example, reference points $446_1$ and $446_3$ on the boundary between sclera 445 and eyelids $442_U$, $442_L$ are identified, but reference points $446_2$ and $446_4$ are not. Nonetheless, reference points $446_1$ and $446_3$ may be used, e.g., in combination with reference point $430_1$ (as depicted in FIG. 4B) or in combination with reference point $430_2$, to determine a measure of eye openness. In some examples, the vertical distance between reference points $446_1$ and $446_3$ may be used in combination with a horizontal distance between the pair of reference points <$446_1$, $446_3$> and reference point $430_1$ (or reference point $430_2$ in other examples) to determine a measure of eye openness. The horizontal distance may provide, for instance, a reference for scale, such that a magnitude of the vertical distance between reference points $446_1$ and $446_3$ may be determined.

FIG. 4C depicts a similar scenario as FIG. 4B, except that instead of reference points reference points $446_1$ and $446_3$ on the left side of cornea 441 being identified, reference points $446_2$ and $446_4$ on the right side of cornea 441 are identified. In some examples, the vertical distance between reference points $446_2$ and $446_4$ may be used in combination with a horizontal distance between the pair of reference points <$446_2$, $446_4$> and reference point $430_1$ (or reference point $430_2$ in other examples) to determine a measure of eye openness. The horizontal distance may provide, for instance, a reference for scale, such that a magnitude of the vertical distance between reference points $446_2$ and $446_4$ may be determined.

Less than all four reference points $434_{1-4}$ may also be used to determine a measure of pupil dilation and/or orientation. For example, in FIG. 4B, reference points $434_1$ and $434_3$, which lie at opposite vertical extents of pupil 444, may be used to determine a measure of pupil dilation and/or orientation. And in FIG. 4C, reference points $434_2$ and $434_4$, which lie at opposite horizontal extents of pupil 444, may be used to determine a measure of pupil dilation and/or orientation.

In some examples, reference points may be calibrated for a particular user. For example, when a new user first puts on HMD 100, a calibration routine may be run that measures various distances between various reference points depicted in FIGS. 3A-C and/or FIGS. 4A-C over time, e.g., the first few minutes of wearing HMD 100. The calibration routine may obtain various baseline measurements, such as distance between medial and lateral commissures of eye 108, vertical distances between various points (e.g., $446_{1-4}$) at the boundary between eyelids and sclera 445, and so forth. These baseline measurement(s) may be used later to determine general scale and/or other measures. For example, a baseline may be established during calibration for the distance between medial and lateral commissures of eye 108. Later, a measured distance between medial and lateral commissures of eye 108 may be compared to this baseline in order to determine a scaling factor to be applied for other measures, such as a measure of eye openness.

Figure 5:
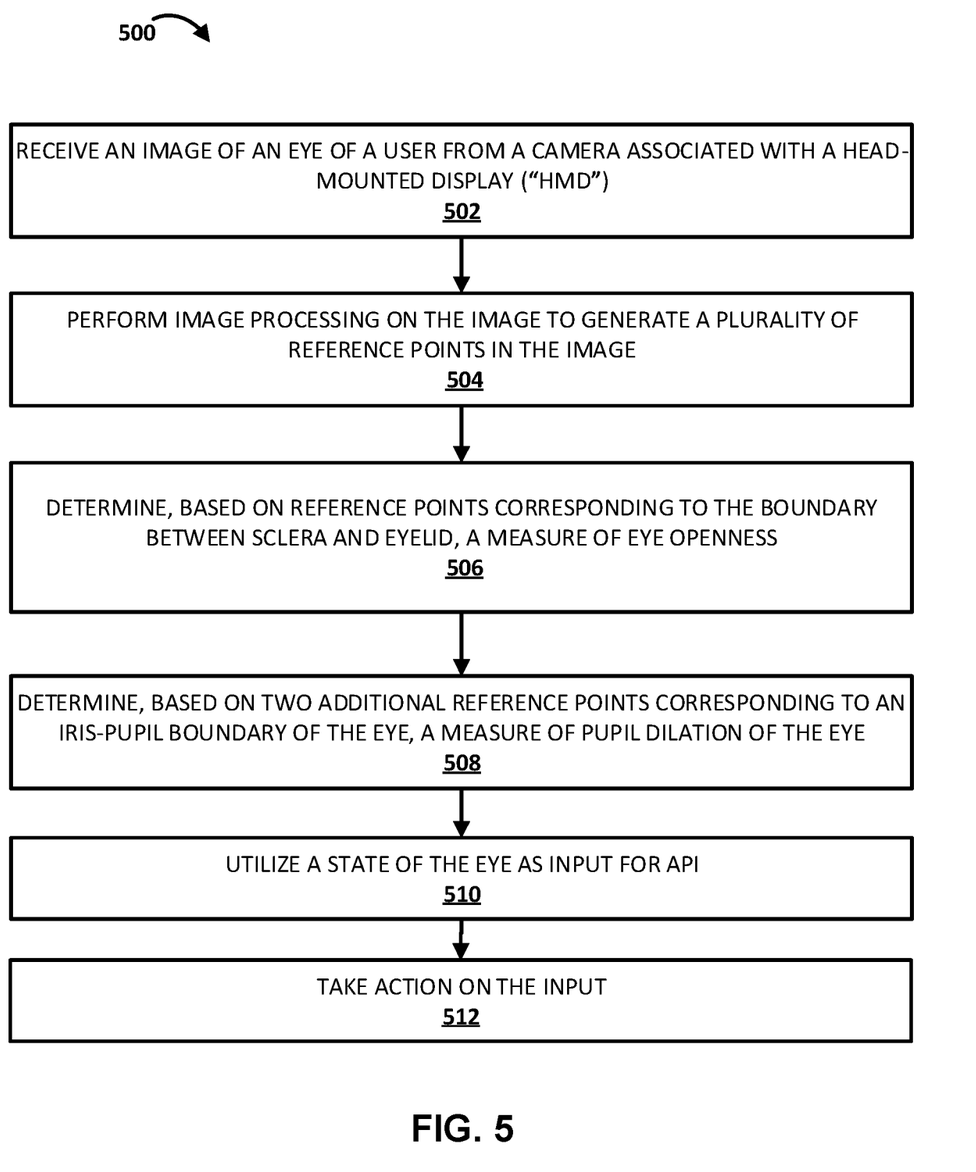
FIG. 5 depicts an example method for practicing selected aspects of the present disclosure.

FIG. 5 illustrates a flowchart of an example method 500 for practicing selected aspects of the present disclosure. The operations of FIG. 5 may be performed by a processor, such as a processor of the various computing devices/systems described herein, including logic 122. For convenience, operations of method 500 will be described as being performed by a system configured with selected aspects of the present disclosure. Other implementations may include additional operations than those illustrated in FIG. 5, may perform operations (s) of FIG. 5 in a different order and/or in parallel, and/or may omit various operations of FIG. 5.

At block 502, the system may receive an image of an eye of a user from vision sensor 114 that is associated with HMD 100. In some examples, such as that depicted in FIG. 1, vision sensor 114 is integral with HMD 100. In other examples, vision sensor 114 may be a separate component, such as an accessory, that may be operably coupled with HMD 100.

At block 504, the system may perform image processing on the image to generate a plurality of reference points in the image. As noted previously, this image processing may take various forms, such as application of the image as input across a trained machine learning model, such as a regression tree model, to infer the plurality of reference points. In some examples, the plurality of reference points include reference points $232_{1-4}$ that correspond to intersections of limbus 340 of eye 108 and an eyelid $342_U$, $342_L$ of the user. In some examples, the reference points may include reference points $446_{1-4}$ along boundaries between the sclera 445 of eye 108 and an eyelid $342_U$, $342_L$ of the user.

At block 506, the system, e.g., by way of eye feature module 222, may determine, based on at least some of the plurality of reference points generated at block 502, various aspects or measurements of the eye 108. In some examples, a subset of the plurality of reference points may be selected based on the desired eye measurement to be taken. For example, all the reference points depicted in FIGS. 3A-C and/or FIGS. 4A-C may be generated, but only those points required for a desired eye measurement, such as eye openness, pupil dilation/orientation, etc., may be selected.

As an example, the system may determine a measure of eye openness using various combinations of multiple reference points. As one example, in FIG. 4B, two reference points 446₁ and 446₃ corresponding to the boundary between sclera 445 and upper and lower eyelids $442_U$, $442_L$, respectively, are used in combination with reference point 330₁ that identifies a left extent of eye 108 to determine a measure of eye openness. As another example, in FIG. 4C, two other reference points 446₂ and 446₄ corresponding to the boundary between sclera 445 and upper and lower eyelids $442_U$, $442_L$, respectively, are used in combination with reference point 330₁ that identifies a left extent of eye 108 to determine a measure of eye openness.

In some examples, eye feature module 222 may determine, based on the reference points corresponding to the intersections of the limbus 340 and the eyelid 342, an orientation of eye 108 of the user. Non-limiting examples of how such orientations could be determined were described previously with respect to FIGS. 3A-C.

At block 508, the system may determine, based on two additional reference points corresponding to an iris-pupil boundary of the eye, such as two of reference points $334_{1-4}$ in FIGS. 3A-C, a measure of pupil dilation of eye 108.

At block 510, the system may utilize a state of the eye that includes one or both of the measure of eye openness determined at block 506 and the measure of pupil dilation determined at block 508, as input, e.g., for an API. As a non-limiting example, the measure of eye openness may be used to estimate a mental or physical state of the user, such as whether the user is tired, is having trouble viewing content rendered on a display, and so forth. The fact that the user is having trouble viewing content rendered on the display may suggest the content is blurry or distorted. This could be caused by a variety of factors, such as HMD 100 being improperly mounted on the user's head, or being calibrated for a different user having a different sized and/or shaped head. Another use of a measure of eye openness may be to control the level of eye openness of a virtual avatar rendered by HMD 100. For example, if the user squints, the virtual avatar squints. If the user's eyes are wide open, the avatar's eyes are wide open. If the user is predicted to be fatigued based on their measure of eye openness, the avatar may be rendered as having a fatigued appearance. And so on. The measure of pupil dilation may be used for the same or different purposes, such as inferring an emotional state of the user, a level of cognitive load, etc.

At block 512, the system may take various actions based on the input used at block 510. For example, if it is estimated that the user is tired, the system may render audible or visual output suggesting that the user take a break, take a nap, get some rest, etc. If it is determined that the user is having trouble viewing rendered content, the system may take various actions, such as performing a stereo imaging calibration routine, providing output suggesting the user reorient HMD 100 on their head, and so forth.

Figure 6:
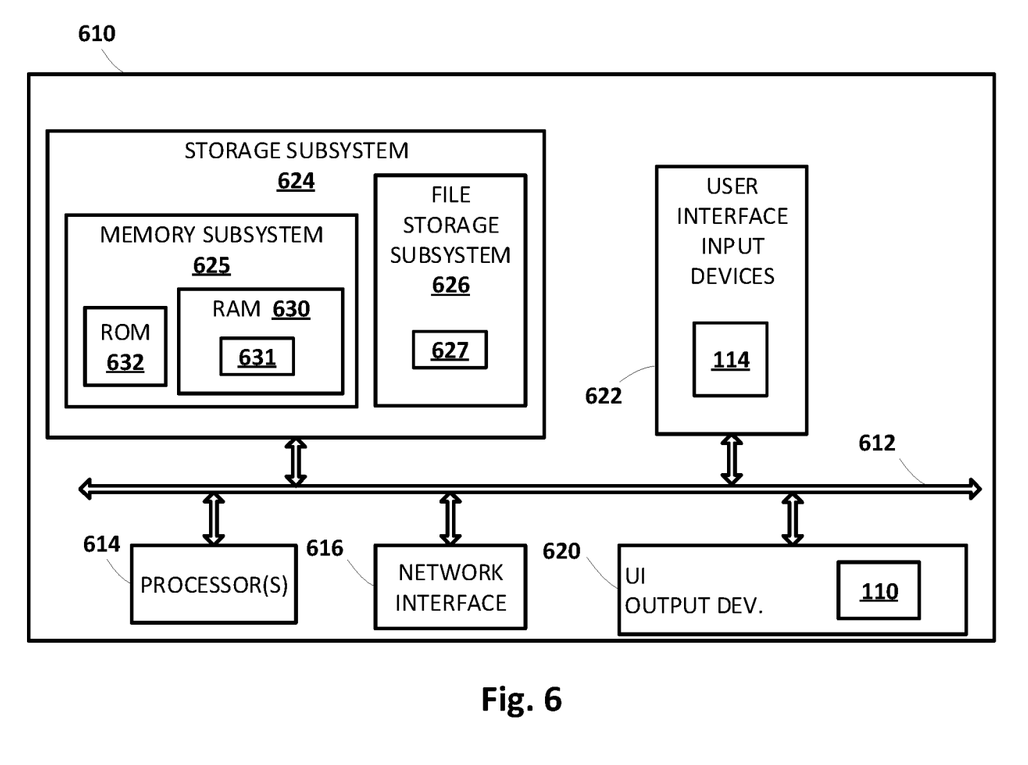
FIG. 6 shows a schematic representation of a computing device, according to an example of the present disclosure.

FIG. 6 is a block diagram of an example computer system 610, which in some examples be representative of components found on HMD 100. Computer system 610 may include at least one processor 614 which communicates with a number of peripheral devices via bus subsystem 612. These peripheral devices may include a storage subsystem 626, including, for example, a memory subsystem 625 and a file storage subsystem 626, user interface output devices 620, user interface input devices 622, and a network interface subsystem 616. The input and output devices allow user interaction with computer system 610. Network interface subsystem 616 provides an interface to outside networks and is coupled to corresponding interface devices in other computer systems.

User interface input devices 622 may include input devices such as a keyboard, pointing devices such as a mouse, trackball, a touch interaction surface, a scanner, a touchscreen incorporated into the display, audio input devices such as voice recognition systems, microphones, vision sensor 114, and/or other types of input devices. In general, use of the term "input device" is intended to include all possible types of devices and ways to input information into computer system 610 or onto a communication network.

User interface output devices 620 may include a display subsystem that includes left and right displays 110L, 110R, a printer, a fax machine, or non-visual displays such as audio output devices. The display subsystem may include a cathode ray tube ("CRT"), a flat-panel device such as a liquid crystal display ("LCD"), a projection device, or some other mechanism for creating a visible image. The display subsystem may also provide non-visual display such as via audio output devices. In general, use of the term "output device" is intended to include all possible types of devices and ways to output information from computer system 610 to the user or to another machine or computer system.

Storage subsystem 624 stores machine-readable instructions and data constructs that provide the functionality of some or all of the modules described herein. These machine-readable instruction modules are generally executed by processor 614 alone or in combination with other processors. Memory 625 used in the storage subsystem 624 may include a number of memories.

For example, a main random access memory ("RAM") 630 may be used during program execution to store, among other things, instructions 631 for detecting and using eye features as described herein. Memory 625 used in the storage subsystem 624 may also include a read-only memory ("ROM") 632 in which fixed instructions are stored.

A file storage subsystem 626 may provide persistent or non-volatile storage for program and data files, including instructions 627 for detecting and using eye features as described herein, and may include a hard disk drive, a floppy disk drive along with associated removable media, a CD-ROM drive, an optical drive, or removable media cartridges. The modules implementing the functionality of certain implementations may be stored by file storage subsystem 626 in the storage subsystem 626, or in other machines accessible by the processor(s) 614.

Bus subsystem 612 provides a mechanism for letting the various components and subsystems of computer system 610 communicate with each other as intended. Although bus subsystem 612 is shown schematically as a single bus, other implementations of the bus subsystem may use multiple busses.

Computer system 610 may be of varying types including a workstation, server, computing cluster, blade server, server farm, or any other data processing system or computing device. Due to the ever-changing nature of computers and networks, the description of computer system 610 depicted in FIG. 6 is intended only as a specific example for purposes of illustrating some implementations. Many other configurations of computer system 610 are possible having more or fewer components than the computer system depicted in FIG. 6.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example of the disclosure along with some of its variations. The terms, descriptions and figures used herein are set forth by way of illustration only and are not meant as limitations. Many variations are possible within the scope of the disclosure, which is intended to be defined by the following claims—and their equivalents—in which all terms are meant in their broadest reasonable sense unless otherwise indicated.

What is claimed is:

1. A method implemented using a processor, comprising:
    receiving an image of an eye of a user from a vision sensor associated with a head-mounted display ("HMD");
    performing image processing on the image by applying the image as input across a trained machine learning model to generate an output comprising a plurality of reference points in the image, wherein the plurality of reference points correspond to a boundary between a sclera of the eye and an eyelid of the user; and
    detecting, based on the plurality of reference points corresponding to the boundary between the sclera and the eyelid, a measure of the eye of the user.

2. The method of claim 1, wherein the measure of the eye includes a measure of eye openness of the user.

3. The method of claim 2, wherein the measure of eye openness is determined based on a distance between two of the reference points corresponding to the boundary between the sclera and the eyelid.

4. The method of claim 3, wherein the measure of eye openness is further determined based on an additional reference point corresponding to a medial or lateral commissure of the eye.

5. The method of claim 1, wherein the machine learning model comprises a regression tree model.

6. The method of claim 1, comprising determining, based on two additional reference points corresponding to an iris-pupil boundary of the eye, a measure of pupil dilation of the eye or an orientation of the pupil.

7. The method of claim 1, comprising:
    determining a mental or physical state of the user based on the measure of eye openness; and
    generating and providing output based on the determined mental or physical state.

8. A head-mounted display ("HMD"), comprising:
    a vision sensor;
    logic operably coupled with the vision sensor, wherein the logic is to:
        perform image processing on an image of an eye of a wearer of the HMD from the vision sensor to generate a plurality of reference points in the image, wherein the plurality of reference points comprise a first reference point corresponding to a boundary between a sclera of the eye and an eyelid of the wearer and a second reference point corresponding to a medial or lateral commissure of the eye;
        detect a measure of eye openness of the wearer based on the plurality of reference points; and
        determining, based on two additional reference points corresponding to an iris-pupil boundary of the eye, a measure of pupil dilation of the eye.

9. The HMD of claim 8, wherein the image processing comprises applying the image as input across a trained machine learning model to generate output, wherein the output indicates the plurality of reference points in the image.

10. The HMD of claim 9, wherein the machine learning model comprises a regression tree model.

11. The HMD of claim 8, wherein the measure of eye openness is determined based on a distance between the plurality of reference points.

12. A non-transitory computer-readable medium comprising instructions that, in response to execution of the instructions by a processor, cause the processor to:
    generate a plurality of reference points by processing an image of an eye of a user from a vision sensor, wherein at least some of the plurality of reference points correspond to a boundary between a sclera of the eye and an eyelid of the user;
    detect, based on the reference points corresponding to the boundary between the sclera and the eyelid, a desired measure of the eye of the user; and select, from the plurality of reference points, a subset of reference points, wherein the subset is selected based on the desired measure of the eye of the user.

\* \* \* \* \*